United States Patent [19]

Bull et al.

[11] 4,202,216
[45] May 13, 1980

[54] ULTRASONIC TESTING

[75] Inventors: Reginald B. Bull, Thatcham; Colin Duffill, Abingdon; Ronald A. Usmar, Didcot, all of England

[73] Assignee: British Gas Corporation, London, England

[21] Appl. No.: 933,032

[22] Filed: Aug. 11, 1978

[30] Foreign Application Priority Data

Aug. 23, 1977 [GB] United Kingdom ............... 35354/77

[51] Int. Cl.² ............................................. G01N 29/04
[52] U.S. Cl. ..................................................... 73/639
[58] Field of Search .................. 73/639, 635, 637, 638, 73/640

[56] References Cited

U.S. PATENT DOCUMENTS

| | | | |
|---|---|---|---|
| 3,371,524 | 3/1968 | Wloszek | 73/639 |
| 3,628,374 | 12/1971 | Laudien et al. | 73/639 |
| 3,628,375 | 12/1971 | Pagano | 73/639 |
| 4,055,990 | 11/1977 | Topping | 73/638 |

FOREIGN PATENT DOCUMENTS

| | | | |
|---|---|---|---|
| 1118141 | 6/1968 | United Kingdom | 73/639 |
| 1294404 | 10/1972 | United Kingdom | 73/639 |

*Primary Examiner*—Stephen A. Kreitman
*Attorney, Agent, or Firm*—Watson, Cole, Grindle & Watson

[57] ABSTRACT

Disclosed is a wheel probe for use on a pipe inspection vehicle. The wheel probe comprises a annular perspex outer rim with a polyurethane tire mounted on a hub assembly which, with the hub, defines a fluid-tight chamber containing an acoustic coupling fluid. A number of ultrasonic transducers are located inside the chamber and are positioned close to the inside circumferential surface of the rim. The hub assembly is carried by a spring loaded carriage which is secured through which ultrasound will pass.

The wheel probe includes a guide wheel on each side. The guide wheels are carried by the carriage but are moveable bodily relative to the center of the hub assembly, and when deflected, they operate on the assembly to move the wheel probe to ensure that the outer rim of the wheel is correctly aligned relative to the pipe.

The wheel probe has a number of shields spaced around its periphery. The gaps between the shields define operating "windows" through which the rim of the wheel probe projects to contact the pipe. The shields are located close to the bore of the pipe so that if the probe encounters an obstruction the shield snags on the obstruction, is pulled between the rim and the pipe to lift the wheel over the obstruction, and turns on to the next operating "window."

Cam followers are provided to hold the shields in position.

10 Claims, 4 Drawing Figures

ULTRASONIC TESTING

BACKGROUND OF THE INVENTION

The present invention relates to wheel probes for insertion into the bore of a pipe for the purpose of ultrasonically inspecting the wall of the pipe.

Known forms of such wheel probes usually comprise a hollow wheel assembly having a soft deformable or inflatable tire around its outer circumference, and ultrasonic transducers located within the wheel assembly for directing and receiving ultrasonic energy through the tire which is urged into contact with the internal surface of the pipe. An acoustic coupling fluid is provided between the tire and the pipe surface to provide transmission of the ultrasonic energy.

It has been found that existing wheel probes are unsatisfactory for certain kinds of applications with which the present invention is particularly concerned, namely, the non-destructive testing of gas or other pipelines in which the wheel probes are carried on an inspection vehicle which is propelled at high speed by the fluid flow in the pipeline, and which encounters obstructions such as weld rings or branch pipe openings likely to cause damage to the wheel probes. Furthermore, it is essential in such applications that adequate acoustic coupling is maintained between the relative moving parts of the wheel probe, and that the outer rim of the wheel is correctly aligned relative to the internal surface of the pipe.

SUMMARY OF THE INVENTION

An object of the present invention is to provide an improved wheel probe designed to remedy the aforesaid disadvantages and limitations of known wheel probes.

According to the present invention there is provided a wheel probe for insertion into the bore of a pipe for the purpose of ultrasonically inspecting the wall of the pipe, the wheel probe comprising a main wheel assembly comprising a solid annular rim made of a material through which sound will pass, and side members which together with the rim define a hollow chamber, an ultrasonic transducer located within the chamber and positioned therein for directing and receiving sound through the rim, the main wheel assembly being mounted for rotation about its central axis in a first mounting member which is itself mounted in a second mounting member for pivotal movement about an axis which extends in a direction normal to the central axis of the main wheel assembly, and a guide wheel located each side of the main wheel assembly, the guide wheels being movable bodily independently of the main wheel assembly and being mounted on the first mounting member for pivotal movement in unison about an axis which is parallel to the central axis of the main wheel assembly, and being operable when one or both of the guide wheels is deflected to move the first mounting member, and hence the main wheel assembly, about the said axis which extends in a direction normal to the central axis of the main wheel assembly.

Preferably there is provided a shield member around the periphery of the main wheel assembly comprising a hollow cylindrical body, or a hollow truncated spheroidal body, located concentrically with the main wheel assembly for rotation about the central axis of the main wheel assembly, the shield member having a plurality of openings through which part of the periphery of the rim protrudes.

Preferably the shield is biased to assume predetermined angular positions about its axis of rotation until deflected by encountering an obstruction in the bore of the pipe. For example, cam followers may be provided which locate in recesses in the periphery of the shield member to hold the shield member in a predetermined angular position.

Preferably the chamber is fluid-tight and an acoustic coupling medium, such as for example, a mixture of glycerol and water with solid particles, for example, graphite or molybdenum disulphide in suspension is contained within the chamber, at least in the region between the transducer and the rim.

More than one transducer may be provided in the chamber.

A flexible deformable solid tire made of a material through which sound will pass (for example polyurethane, polythene, or a rubber compound) may be provided around the periphery of the rim.

The inside circumferential surface of the annular rim may be shaped so as to be parallel to the transmitting and receiving surfaces of the transducer or transducers, although preferably, the transducer or transducers may be spaced away from the inside circumferential surface of the annular rim and a suitably shaped block made of a material through which sound will pass, and which conforms with the sound transmitting or receiving face of the transducer and the inner circumferential surface of the rim, may be located between the transducer and the rim and any space between the block and the rim being filled with a film of said acoustic coupling medium through which ultrasound will pass.

Alternatively, the transducer or transducers may be spaced away from the inside surface of the rim and the space between the transducer and the rim filled with coupling medium through which ultrasound will pass.

BRIEF DESCRIPTION OF THE DRAWINGS

An embodiment of the present invention will now be described, by way of an example, with reference to the accompanying drawings in which.

DETAILED DESCRIPTION OF THE PREFERRED EMBODIMENTS

Figure 1:
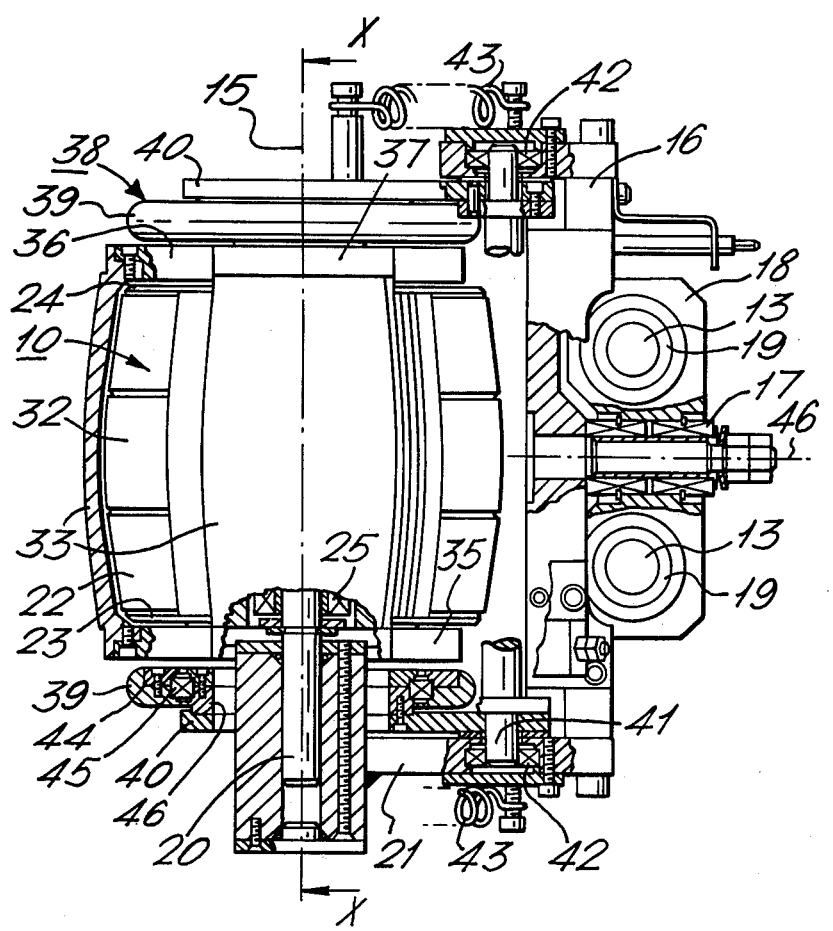
FIG. 1 is a plan view, partly in section, of a wheel probe constructed in accordance with the present invention.
Figure 2:
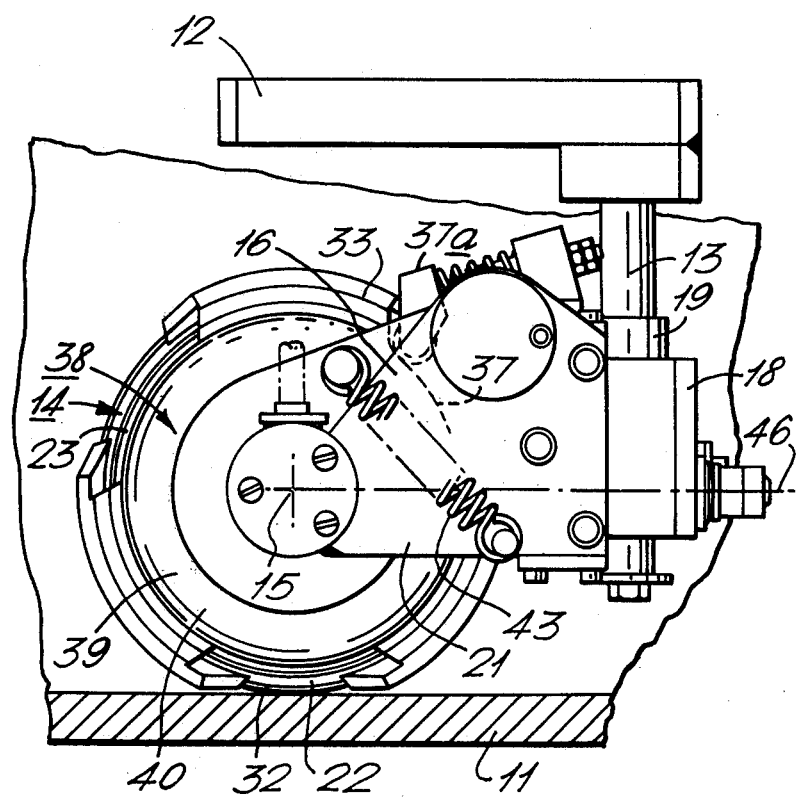
FIG. 2 is a side elevation of the wheel probe of FIG. 1.

Referring to the drawings, there is shown a wheel probe 10 for insertion into a bore of pipe 11. A number of such probes 10 are mounted on a remotely controlled vehicle which is caused to travel along the bore of the pipe 11. Each wheel probe 10 is secured to the vehicle by means of a support member 12 which is fixed securely to the vehicle. The support member 12 has two shafts 13 which, in use, extend in a radial direction with respect to the pipe 11.

The wheel probe 10 comprises main wheel assembly 14 mounted for rotation about axis 15 in a first mounting member 16 which is itself mounted in a bearing 17 in a second mounting member 18 for rotation about an axis normal to the axis of rotation of the main wheel assembly 14. The second mounting member 18 is mounted on the shafts 13 by way of two linear bearings 19 which allow it to slide along the shafts 13.

The main wheel assembly 14 is mounted for rotation on the free end of a fixed spindle 20 which is secured at one of its ends to a slide member 21 of the first mounting member 16. The main wheel assembly 14 is shown in greater detail in FIGS. 3 and 4 and comprises a hollow housing made up of a solid annular rim 22 made of Perspex (A Registered Trade Mark) and two end plates 23, 24 which are mounted on bearings 25 on the spindle 20 so as to be freely rotatable on the spindle 20. Oil seals 26 are provided between the end plates 23, 24 and the spindle 20 and "O" ring seals are provided between the end plates 23, 24 and the rim 22. An ultrasonic probe assembly 27 is resiliently carried by the spindle 20 and the hollow housing so formed contains an acoustic coupling medium (not shown) such as, for example, a mixture of glycerol and water loaded with particles of carbon, for example graphite, or molybdenum disulphide. The size of the particles is chosen to be such as not to attenuate sound of the frequency produced by a given transducer or transducers of the ultrasonic probe assembly with which the medium is used, but at the same time to attenuate sound of other unwanted frequencies.

The ultrasonic probe assembly 27 comprises a support structure, consisting of brackets 28 and rods 28a, which is arranged to support a nylon block 29 upon which are mounted a plurality of transducers 31, for transmitting ultrasound into the wall of the pipe 11 and for receiving sound scattered or reflected from the wall of the pipe 11. The block 29 is urged against the inside surface of the rim 22 by a tension spring 30 which is anchored between one of the brackets 28 and a pin secured in a central block 20a which forms part of the spindle 20. The rods 28a are slidably supported in the spindle block 20a for linear movement of the probe assembly. The block 29 is shaped to conform with the shape of the inside surface of the rim 22, so as to ensure that the beams of sound from the transducers 31 enter the pipe wall at a predetermined preferred angle, and that the acoustic coupling medium is permitted to penetrate any gaps between the transducers 31 and the block 29 and between the block 29 and the rim 22. Electrical leads (not shown) from the transducers 31 pass along a bore (not shown) in the spindle 20 through seals which prevent the acoustic coupling medium leaking from the wheel assembly.

The outer rim 22 is barrel shaped, that is to say that it has a curved profile in a direction along the axis of rotation, and is provided with a tight-fitting, flexible deformable tire 32 made of, for example, polyurethane or other material which will transmit sound.

Around the wheel assembly is a close-fitting independently rotatable shield 33. The shield 33 has three windows through which projects a sector of the wheel assembly 14. The shield 33 is mounted on the outer race of ball bearings 34, the inner races of which are secured to the end plates 23, 24 of the wheel assembly 14 by end plates 35, 36. The outer circumference of the shield 33 at each side of the shield has a number of recesses 37 into which locate spring biased cam-followers 37a which ensure that the shield 33 assumes a preferred orientation where any one of the windows is located alongside the block 29 so that a portion of the wheel assembly adjacent the block 29 projects through one of the windows.

The edges of each window are shaped so that in normal use the wheel assembly contacts the pipe wall and the shield 33 is just clear of the surface of the wall of the pipe 11. In the event that the wheel assembly 14 encounters an obstruction, such as, for example a weld region, which could damage the rim 22 or tire 32, the shield 33 snags (with the help of serrations or grooves) on the obstruction and is rotated to pass between the rim 22 and the pipe 11, at the same time overriding the cam-followers which locate in recesses 37. In this way the rim 22 is lifted clear of the obstruction until the next window around the shield 33 is located adjacent the block 29, whereupon the cam followers locate in fresh recesses 37 to hold the shield 33 with a window adjacent the block 29.

The first mounting member 16 also carries a guide wheel assembly 38. The guide wheel assembly 38 comprises two guide wheels 39 each mounted on a side arm 40 which is itself secured to a shaft 41 which is mounted in bearings 42 in the side member 21 of the first mounting member 16.

The guide wheel assembly 38 pivots about the longitudinal axis of the shaft 41 and is suspended on two springs 43 fixed to the side members 21 of the first mounting member 16.

The guide wheels 39 are made of metal and comprise an outer rim 44 mounted on ball bearings 45 carried by a plate 46 which is bolted to the side members 40. The axes of rotation of the guide wheels 39 are co-axial with the axis 15 of the main wheel assembly 14 and the guide wheels 39 are of slightly smaller diameter than the diameter of the rim 22.

In operation, the wheel probe 10 is positioned in the bore of pipe 11 with the axis 46, about which the first mounting member 16 pivots, aligned with the longitudinal axis of the bore of pipe 11 so that the tire 32 on the outer rim 22 is pressed into intimate contact with the bore of pipe 11 at a point on a line which is aligned with the longitudinal axis of the pipe 11 by compression springs (not shown) of the shafts 13.

The guide wheels 39 also touch the wall of the pipe 11, and therefore with the main wheel assembly 14 provides three points of contact with the pipe in a common plane which is transverse to the bore of the pipe 11. If the wheel probe 10 is offered up to the pipe 11 and is not in the correct position, one guide wheel 39 will be at a slightly higher position in the bore and will tilt the first mounting member 16 about axis 46 to align the rim 22 of the main wheel assembly 14 at the correct position where the rim 22, and hence block 29, is arranged so that it is exactly normal to a tangent to the wall of the pipe 11 at the point of contact.

Figure 3:
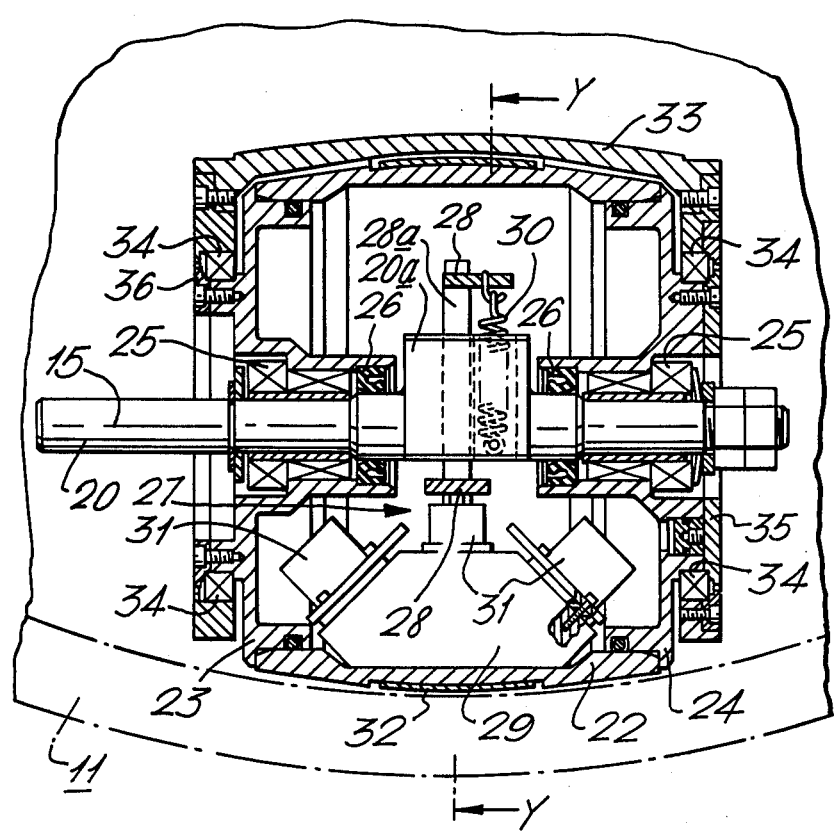
FIG. 3 is an elevation of the main wheel assembly of the wheel probe of FIG. 1 sectioned along line X—X of FIG. 1.
Figure 4:
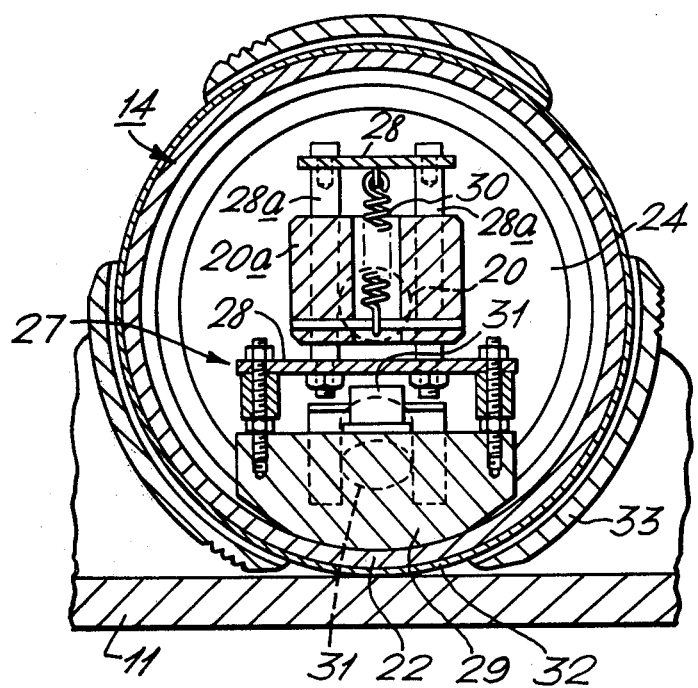
FIG. 4 is a sectional view of the main wheel assembly of FIG. 3 sectioned along line Y—Y of FIG. 3.

In an alternative wheel probe arrangement in accordance with the invention, the transducers 31 are securely (rather than resiliently) supported by the spindle 20, 20a in the positions shown in FIGS. 3 and 4, but the block 29 is omitted and acoustic coupling of ultrasound between the transducers and the internal surface of the rim 22 is achieved by said acoustic coupling medium which fills the space therebetween.

We claim:

1. A wheel probe for insertion into the bore of a pipe for the purpose of ultrasonically inspecting the wall of the pipe, the wheel probe comprising a main wheel assembly comprising a solid annular rim made of a material through which sound will pass, and side members which together with the rim define a hollow chamber, at least one ultrasonic transducer located within the chamber and positioned therein for directing and receiving sound through the rim, first and second mounting members, the main wheel assembly being mounted for rotation about its central axis in the first mounting member which is itself mounted in the second mounting member for pivotal movement about a first axis which extends in a direction normal to the central axis of the main wheel assembly, and a guide wheel located on each side of the main wheel assembly, the guide wheels being movable bodily independently of the main wheel assembly and being mounted on the first mounting member for pivotal movement in unison about a second axis which is parallel to the central axis of the main wheel assembly, and being operable when one or both of the guide wheels is deflected to move the first mounting member and hence the main wheel assembly about said first axis which extends in a direction normal to the central axis of the main wheel assembly.

2. A wheel probe as claimed in claim 1, wherein a shield member is provided around the periphery of the main wheel assembly, the shield member comprising a hollow cylindrical body, or a hollow truncated spheroidal body, located concentrically with the main wheel assembly for rotation about the central axis of the main wheel assembly, the shield member having a plurality of openings through which part of the periphery of the rim of the main wheel assembly protrudes.

3. A wheel probe as claimed in claim 2, wherein the shield member is biased by biasing means to assume predetermined angular positions about its axis of rotation until deflected by encountering an obstruction in the bore of the pipe.

4. A wheel probe as claimed in claim 3, wherein the biasing means comprises cam followers which locate in recesses in the periphery of the shield member to hold the shield member in said predetermined angular position.

5. A wheel probe as claimed in any preceding claim, wherein said hollow chamber is fluid tight and contains a liquid acoustic coupling medium through which ultrasound will pass.

6. A wheel probe as claimed in claim 5, wherein the transducer is spaced away from the inside circumferential surface of the annular rim and a suitably shaped block made of a material through which sound will pass and which conforms with the sound transmitting or receiving face of the transducer and the inner circumferential surface of the rim, is located between the transducer and the rim, and any space between the block and the rim is filled with a film of said acoustic coupling medium.

7. A wheel probe as claimed in claim 5, wherein the transducer is spaced away from the inside surface of the rim and the space between the transducer and the rim is filled with said acoustic coupling medium.

8. A wheel probe as claimed in claim 5, wherein said coupling medium is a mixture of glycerol and water with graphite or molybdenum disulphide particles in suspension.

9. A wheel probe as claimed in claim 1, wherein a flexible deformable solid tire of a material through which ultrasound will pass is provided around the periphery of the rim.

10. A wheel probe as claimed in claim 9, wherein said tire is made of polyurethane, polythene or a rubber compound.

* * * * *